(12) United States Patent
Dannenberg et al.

(10) Patent No.: US 6,403,630 B1
(45) Date of Patent: Jun. 11, 2002

(54) TREATING CANCERS ASSOCIATED WITH OVEREXPRESSION OF HER-2/NEU

(75) Inventors: Andrew J. Dannenberg, New York; Kotha Subbaramaiah, Flushing, both of NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 09/868,617

(22) PCT Filed: Jan. 10, 2000

(86) PCT No.: PCT/US00/00007

§ 371 (c)(1),
(2), (4) Date: Jun. 22, 2001

(87) PCT Pub. No.: WO00/44225

PCT Pub. Date: Aug. 3, 2000

Related U.S. Application Data

(60) Provisional application No. 60/117,466, filed on Jan. 27, 1999.

(51) Int. Cl.[7] ..................... A61K 31/415; A61K 39/395
(52) U.S. Cl. ................. 514/406; 514/210.01; 514/247; 514/252; 514/341; 514/365; 514/372; 514/374; 514/378; 514/399; 514/400; 514/403; 514/407; 514/602; 514/603; 514/604; 514/605; 514/709; 424/138.1; 424/155.1; 424/174.1
(58) Field of Search ........................... 514/210.01, 247, 514/252, 341, 365, 372, 374, 378, 399, 400, 403, 406, 407, 602, 603, 604, 605, 709; 424/138.1, 155.1, 174.1

(56) References Cited

U.S. PATENT DOCUMENTS

| | | | |
|---|---|---|---|
| 5,288,477 A | 2/1994 | Bacus | 424/2 |
| 5,514,554 A | 5/1996 | Bacus | 435/7.23 |
| 5,677,171 A | 10/1997 | Hudziak et al. | 435/240.27 |
| 5,720,937 A | 2/1998 | Hudziak et al. | 424/9.34 |
| 5,731,343 A | 3/1998 | Feng et al. | 514/450 |
| 5,770,195 A | 6/1998 | Hudziak et al. | 424/130.1 |
| 5,772,997 A | 6/1998 | Hudziak et al. | 424/130.1 |
| 5,776,967 A | 7/1998 | Kreft et al. | 514/411 |
| 5,783,186 A | 7/1998 | Arakawa et al. | 424/143.1 |
| 5,783,404 A | 7/1998 | Koski | 435/7.23 |
| 5,792,986 A * | 8/1998 | Seibert et al. | 514/406 |
| 5,824,699 A | 10/1998 | Kreft et al. | 514/411 |
| 5,830,911 A | 11/1998 | Failli et al. | 514/411 |
| 5,846,538 A | 12/1998 | Cheever et al. | 424/185.1 |
| 5,858,694 A | 1/1999 | Piazza et al. | 435/19 |
| 5,972,986 A | 10/1999 | Seibert et al. | 514/406 |

OTHER PUBLICATIONS

Reese, D. M., et al., Stem Cells 15:1–8 (1997).
McNeil, C., NCI publication downloaded from WEB prior to Jan. 16, 1999 denoted cancer Trials/Herceptin Proves itself in Advanced Breast Cancer, Raises its Sites.

* cited by examiner

*Primary Examiner*—Frederick Krass

(57) ABSTRACT

Cancers associated with overexpression of HER-2/neu are treated with a selective inhibitor of cyclooxygenase-2 as the sole treating agent or said inhibitor in combination regimen with HERCEPTIN® and/or standard therapy. Uses include adjuvant therapy for HER-2/neu positive breast cancer and treatment of HER-2/neu positive breast cancer that has metastasized.

10 Claims, No Drawings

TREATING CANCERS ASSOCIATED WITH OVEREXPRESSION OF HER-2/NEU

This application is a filing under 35 U.S.C. 371 of PCT/US00/00007, filed on Jan. 10, 2000, which claims the benefit of U.S. Provisional Application No. 60/117,466, filed on Jan. 27, 1999; PCT/US00/00007 has been published under No. WO 00/44225, and the publication is in English.

This invention was made at least in part with United States Government support under National Institutes of Health grant CA68136. The United States Government has certain rights in the invention.

TECHNICAL FIELD

This invention is directed to treatment of HER-2/neu overexpressing cancers.

BACKGROUND OF THE INVENTION

The HER-2/neu (erbB-2) gene product is a 185-kDA transmembrane receptor tyrosine kinase that belongs to the family of receptors for epidermal growth factor. It is described in some detail in Reese, D. M., et al., Stem Cells, 15, 1–8 (1997) which is incorporated herein by reference.

Recently, enormous attention has been given to the importance of HER-2/neu in breast cancer. HER-2/neu is overexpressed in 20–30% of human breast cancers and the increased expression has been associated with poor prognosis. The discovery of this has led to the development of HERCEPTIN®, an antibody to HER-2/neu, which in tests has been found to lengthen remission time in metastatic breast cancer. HER-2/neu is a cell-surface receptor that transmits growth signals to the cell nucleus. HERCEPTIN® appears to block these signals thereby apparently inhibiting proliferation of cells mediated by HER-2/neu in HER-2/neu positive breast cancer.

Overexpression of HER-2/neu has also been found in a portion of ovarian cancers, gastric cancers, endometrial cancers, salivary cancers, pancreatic cancers, prostate cancers, colorectal cancers, and non-small-cell lung cancers. The other cancers associated with overexpression of HER-2-neu are potentially treatable with HERCEPTIN®.

SUMMARY OF THE INVENTION

The invention herein is directed to treating cancers associated with overexpression of HER-2/neu with agent different from HERCEPTIN® or as a supplement to HERCEPTIN® to block the pathological results of HER-2/neu overexpression and thereby inhibit the development of cancers associated with overexpression of HER-2/neu.

It is shown herein that HER-2/neu expression causes increase of c-Jun and it is posited that the c-Jun induces cyclooxygenase-2 (COX-2) gene expression via the cyclic AMP response element and that this results in overexpression of COX-2 which mediates tumor formation. It is concluded from this that cancers associated with overexpression of HER-2/neu expression are beneficially treated with selective inhibitors of cyclooxygenase-2.

In a broad embodiment, the invention is directed at a method of treating cancer associated with overexpression of HER-2/neu in a patient affected with this condition, comprising administering to said patient a therapeutically effective amount of a selective inhibitor of cyclooxygenase-2. The cyclooxygenase-2 inhibitor can be administered as the only therapy or in a combination regimen with a therapeutically effective amount of HERCEPTIN®, a HER-2/neu antibody available from Genentech, and/or conventional therapy for the kind of cancer being treated.

In a narrower embodiment, the invention is directed at a method of treating breast cancer associated with overexpression of HER-2/neu in a patient affected with this condition comprising administering to said patient a therapeutically effective amount of a selective inhibitor of cyclooxygenase-2. The cyclooxygenase-2 inhibitor can be administered for or as part of adjuvant therapy for HER-2/neu positive breast cancer or for treatment of or as part treatment of HER-2/neu positive breast cancer that has metastasized. The cyclooxygenase-2 inhibitor is preferably administered in a combination regimen with HERCEPTIN® and preferably also is administered in combination regimen with standard chemotherapy or endocrine therapy or radiation treatment.

The term "cancer associated with overexpression of HER-2/neu" is used herein to mean that cancerous tissue contains more HER-2/neu than non-cancerous tissue from the same portion of the body.

The term "HER-2/neu positive breast cancer" is used herein to mean breast cancer associated with overexpression of HER-2/neu.

DETAILED DESCRIPTION

The cancers associated with overexpression of HER-2/neu include all those cancers where overexpression of HER-2/neu is found in cancerous tissue and comprise breast cancers, ovarian cancers, gastric cancers, endometrial cancers, salivary cancers, pancreatic cancers, prostate cancers, colorectal cancers and non-small-cell lung cancers, where overexpression of HER-2/neu is found in the cancerous tissue.

Assays for HER-2/neu overexpression have been developed or are under development. These include the Vysis PathVysion HER2 DNA Probe Kit developed by Vysis Inc., Downer's Grove, Ill., which is based on fluorescent in situ hybridization and a diagnostic kit being developed by DAKO A/S of Glostrup, Denmark which is directed to detecting antibodies to the HER-2/neu protein based on immunohistochemistry.

We turn now to the selective inhibitors of cyclooxygenase-2. The selective inhibitors of cyclooxygenase-2 are synthetic compounds.

The selective inhibitors of cyclooxygenase-2 are preferably those where the ratio of the $IC_{50}$ concentration for cyclooxygenase-1 to the $IC_{50}$ concentration for cyclooxygenase-2 is 5 or more, very preferably 100 or more.

Selective inhibitors of cyclooxygenase-2 include the following compounds:

(1) 4-[5-(4-Chlorophenyl)-3-(trifluoromethyl)-1H-pyrazol-1-yl]benzenesulfonamide
(2) 4-[5-(4-Bromophenyl)-3-(trifluoromethyl)-1H-pyrazol-1-yl]benzenesulfonamide
(3) 4-[5-(3-Chlorophenyl)-3-(trifluoromethyl)-1H-pyrazol-1-yl]benzenesulfonamide
(4) 4-[5-(4-Methylphenyl)-3-(trifluoromethyl)-1H-pyrazol-1-yl]benzenesulfonamide
(5) 4-[5-(2-Chlorophenyl)-3-(trifluoromethyl)-1H-pyrazol-1-yl]benzenesulfonamide
(6) 4-[5-(4-Trifluoromethylphenyl)-3-(trifluoromethyl)-1H-pyrazol-1-yl]benzenesulfonamide
(7) 4-[5-(4-Fluorophenyl)-3-(trifluoromethyl)-1H-pyrazol-1-yl]benzenesulfonamide
(8) 4-[5-Phenyl-3-(trifluoromethyl)-1H-pyrazol-1-yl]benzenesulfonamide
(9) 4-[5-(4-Methoxyphenyl)-3-(trifluoromethyl)-1H-pyrazol-1-yl]benzenesulfonamide

(10) 4-[5-(4-Trifluoromethoxyphenyl)-3-(trifluoromethyl)-1H-pyrazol-1-yl]benzenesulfonamide
(12) 4-[5-(2-Methylphenyl)-3-(trifluoromethyl)-1H-pyrazol-1-yl]benzenesulfonamide
(12) 4-[5-(4-Chlorophenyl)-3-(difluoromethyl)-1H-pyrazol-1-yl]benzenesulfonamide
(13) 4-[4-(Aminosulfonyl)phenyl]-5-(4-chlorophenyl)-1H-pyrazol-3-carboxylate
(14) 4-[4-(Aminosulfonyl)phenyl]-5-(4-chlorophenyl)-1H-pyrazol-3-carboxamide
(15) 4-[5-(4-[Methylthio]phenyl)-3-(difluoromethyl)-1H-pyrazol-1-yl]benzenesulfonamide
(16) 4-[5-(4-[Methylsulfonyl]phenyl)-3-(difluoromethyl)-1H-pyrazol-1-yl]benzenesulfonamide
(17) 4-[5-(2,4-[Difluoro]phenyl)-3-(trifluoromethyl)-1H-pyrazol-1-yl]benzenesulfonamide
(18) 4-[5-(2,6-[Difluoro]phenyl)-3-(trifluoromethyl)-1H-pyrazol-1-yl]benzenesulfonamide
(19) 4-[5-(4-Cyanophenyl)-3-(trifluoromethyl)-1H-pyrazol-1-yl]benzenesulfonamide
(20) 4-[5-(4-Chlorophenyl)-3-(heptafluoropropyl)-1H-pyrazol-1-yl]benzenesulfonamide
(21) 4-[5-(4-Chlorophenyl)-3-(chloro-difluoromethyl)-1H-pyrazol-1-yl]benzenesulfonamide
(22) 4-[5-(4-Chlorophenyl)-3-(pentafluoroethyl)-1H-pyrazol-1-yl]benzenesulfonamide
(23) 4-[5-(4-Biphenyl)-3-(difluoromethyl)-1H-pyrazol-1-yl]benzenesulfonamide
(24) 4-[5-(4-Pyrazinyl)-3-(difluoromethyl)-1H-pyrazol-1-yl]benzenesulfonamide
(25) 4-[5-(5-Chloro-2-thienyl)-3-(difluoromethyl)-1H-pyrazol-1-yl]benzenesulfonamide
(26) 4-[5-(4-Morpholino)phenyl)-3-(difluoromethyl)-1H-pyrazol-1-yl]benzenesulfonamide
(27) 4-[5-(1-Cyclohexyl)-3-(difluoromethyl)-1H-pyrazol-1-yl]benzenesulfonamide
(28) 4-[5-(5-Bromo-2-thienyl)-3-(difluoromethyl)-1H-pyrazol-1-yl]benzenesulfonamide
(29) 4-[5-(4-Thienyl)-3-(difluoromethyl)-1H-pyrazol-1-yl]benzenesulfonamide
(30) 4-[5-(4-[Trifluoromethyl]phenyl)-3-(difluoromethyl)-1H-pyrazol-1-yl]benzenesulfonamide
(31) 4-[5-(3,4-Dichlorophenyl)-3-(trifluoromethyl)-1H-pyrazol-1-yl]benzenesulfonamide
(32) 4-[5-(2,4-Dichlorophenyl)-3-(trifluoromethyl)-1H-pyrazol-1-yl]benzenesulfonamide
(33) 4-[5-Phenyl-3-(3-hydroxypropyl)-1H-pyrazol-1-yl]benzenesulfonamide
(34) 4-[5-(4-Fluorophenyl)-3-(3-hydroxypropyl)-1H-pyrazol-1-yl]benzenesulfonamide
(35) 4-[4-(Aminosulfonyl)phenyl]-5-(4-fluorophenyl)-1H-pyrazole]-3-propanoic acid
(36) 4,5-Dihydro-4-[3-trifluoromethyl]-1H-benz[g]indazol-1-yl]benzenesulfonamide
(37) 4-[5-(4-Chlorophenyl)-4-chloro-1H-pyrazol-1-yl]benzenesulfonamide
(38) 4-[5-(4-Chlorophenyl)-3-(trifluoromethyl)-4-chloro-1H-pyrazol-1-yl]benzenesulfonamide
(39) 4-[1-(4-Fluorophenyl)-3-(trifluoromethyl)-1H-pyrazol-5-yl]benzenesulfonamide
(40) 1-(2,4,6-Trichlorobenzoyl)-5-methoxy-2-methyl-3-indolyl acetic acid
(41) 1-(2,6-dichlorobenzoyl)-5-methoxy-2-methyl-3-indolyl acetic acid
(42) 3-(4-(Aminosulfonyl)phenyl)-2-(4-fluorophenyl)-5-(2-hydroxy-2-propyl)thiophene
(43) 3-(4-(Aminosulfonyl)phenyl)-2-(4-fluorophenyl)thiophene
(44) 3-(4-(Aminosulfonyl)phenyl)-2-(4-fluorophenyl)-5-(2-propyl)thiophene
(45) 3-(4-(Aminosulfonyl)phenyl)-2-cyclohexylthiophene
(46) 5-(4-Carboxyphenyl)-4-(4-(methylsulfonyl)phenyl)thiophene-2-carboxylic acid
(47) 4-(4-Fluorophenyl)-2-methyl-5-(4-(methylsulfonyl)phenyl)thiazole
(48) 2-(4-Fluorophenyl)-3-(4-(methylsulfonyl)phenyl)-2-cyclopenten-1-one
(49) 4-(4-(Methylsulfonyl)phenyl-5-(4-fluorophenyl)-isothiazole
(50) 3-(4-Fluorophenyl)-4-(4-(methylsulfonyl)phenyl-2-(5H)-furanone
(51) 3-(4-Fluorophenyl)-4-(4-(aminosulfonyl)phenyl)-2-(2H)-furanone
(52) 3-(4-Fluorophenyl)-4-(4-(methylsulfonyl)phenyl)furan
(53) 5,5-Dimethyl-3-(4-fluorophenyl)-4-(4-methylsulfonyl)phenyl)-2-(5H)furanone
(54) 2-((4-Aminosulfonyl)phenyl)-3-(4-fluorophenyl)thiophene
(55) 3-(2,4-Difluorophenyl)-4-(4-(methylsulfonyl)phenyl)-2-(5H)-furanone
(56) 3-(3,4-Difluorophenyl)-4-(4-(methylsulfonyl)phenyl)-2-(5H)-furanone
(57) 3-(2,6-Difluorophenyl)-4-(4-(methylsulfonyl)phenyl)-2-(5H)-furanone
(58) 3-(2,5-Difluorophenyl)-4-(4-(methylsulfonyl)phenyl)-2-(5H)-furanone
(59) 3-(3,5-Difluorophenyl)-4-(4-(methylsulfonyl)phenyl)-2-(5H)-furanone
(60) 3-(4-Bromophenyl)-4-(4-(methylsulfonyl)phenyl)-2-(5H)-furanone
(61) 3-(4-Chlorophenyl)-4-(4-(methylsulfonyl)phenyl)-2-(5H)-furanone
(62) 3-(4-Methoxyphenyl)-4-(4-(methylsulfonyl)phenyl)-2-(5H)-furanone
(63) 3-(Phenyl)-4-(4-(methylsulfonyl)phenyl)-2-(5H)-furanone
(64) 3-(2-Chlorophenyl)-4-(4-(methylsulfonyl)phenyl)-2-(5H)-furanone
(65) 3-(2-Bromo-4-fluorophenyl)-4-(4-(methylsulfonyl)phenyl)-2-(5H)-furanone
(66) 3-(2-Bromo-4-Chlorophenyl)-4-(4-(methylsulfonyl)phenyl)-2-(5H)-furanone
(67) 3-(4-Chloro-2-fluorophenyl)-4-(4-(methylsulfonyl)phenyl)-2-(5H)-furanone
(68) 3-(3-Bromo-4-fluorophenyl)-4-(4-(methylsulfonyl)phenyl)-2-(5H)-furanone
(69) 3-(3-Chlorophenyl)-4-(4-(methylsulfonyl)phenyl)-2-(5H)-furanone
(70) 3-(2-Chloro-4-fluorophenyl)-4-(4-(methylsulfonyl)phenyl)-2-(5H)-furanone
(71) 3-(2,4-Dichlorophenyl)-4-(4-(methylsulfonyl)phenyl)-2-(5H)-furanone
(72) 3-(3,4-Dichlorophenyl)-4-(4-(methylsulfonyl)phenyl)-2-(5H)-furanone
(73) 3-(2,6-Dichlorophenyl)-4-(4-(methylsulfonyl)phenyl)-2-(5H)-furanone
(74) 3-(3-Chloro-4-fluorophenyl)-4-(4-(methylsulfonyl)phenyl)-2-(5H)-furanone
(75) 3-(4-Trifluoromethylphenyl)-4-(4-(methylsulfonyl)phenyl)2-(5H)-furanone
(76) 3-(3-Fluoro-4-methoxyphenyl)-4-(4-(methylsulfonyl)phenyl)-2-(5H)-furanone
(77) 3-(3-Chloro-4-methoxyphenyl)-4-(4-(methylsulfonyl)phenyl)-2-(5H)furanone
(78) 3-(3-Bromo-4-methoxyphenyl)-4-(4-(methylsulfonyl)phenyl)-2-(5H)-furanone

(79) 3-(2-Fluorophenyl)-4-(4-(methylsulfonyl)phenyl)-2-(5H)-furanone
(80) 3-(4-Methylthiophenyl)-4-(4-(methylsulfonyl)phenyl)-2-(5H)-furanone
(81) 3-(3-Fluorophenyl)-4-(4-(methylsulfonyl)phenyl)-2-(5H)-furanone
(82) 3-(2-Chloro-6-fluorophenyl)4-(4-(methylsulfonyl)phenyl)-2-(5H)-furanone
(83) 3-(3-Bromo-4-methylphenyl)-4-(4-(methylsulfonyl)phenyl)-2-(5H)-furanone
(84) 3-(4-Bromo-2-fluorophenyl)-4-(4-(methylsulfonyl)phenyl)-2-(5H)-furanone
(85) 3-(3,4-Dibromophenyl)-4-(4-(methylsulfonyl)phenyl)-2-(5H)-furanone
(86) 3-(4-Chloro-3-fluorophenyl)-4-(4-(methylsulfonyl)phenyl)-2-(5H)-furanone
(87) 3-(4-Bromo-3-fluorophenyl)-4-(4-(methylsulfonyl)phenyl)-2-(5H)-furanone
(88) 3-(4-Bromo-2-chlorophenyl)-4-(4-(methylsulfonyl)phenyl)-2-(5H)-furanone
(89) 3-(2-Naphthyl)-4-(4-(methylsulfonyl)phenyl)-2-(5H)-furanone
(90) 3-(7-Quinolinyl)-4-(4-(methylsulfonyl)phenyl)-2-(5H)-furanone
(91) 3-(3,4-Dichlorophenyl)-4-(4-(aminosulfonyl)phenyl)-2-(2H)-furanone
(92) 3-(3,4-Dichlorophenyl)-4-(4-(aminosulfonyl)phenyl)-2-(2H)-furanone
(93) 3-(3,4-Dichlorophenyl)-4-(4-(aminosulfonyl)phenyl)-2-(2H)-furanone
(94) 3-(3-Bromo-4-methoxyphenyl)4-(4-(aminosulfonyl)phenyl)-2-(2H)furanone
(95) 3-(4-(Methylsulfonyl)phenyl)-2-phenylbenzo[b]furan
(96) 3-(4-Methylsulfonyl)phenyl)-2-phenylbenzo[b]thiophene
(97) 3-(4-Methylsulfonyl)phenyl)-2-phenylinden-1-one
(98) 2-(4-Fluorophenyl)-3-(4-(methylsulfonyl)phenyl)indole
(99) 3-(4-Fluorophenyl)-2-(4-(methylsulfonyl)phenyl)indole
(100) 2-(4-Fluorophenyl)-3-(4-(methylsulfonyl)phenyl)-4H-thieno[2,3-c]-furan-6-one
(101) 2-(3,4-Difluorophenyl)-3-(4-(methylsulfonyl)phenyl)-4H-thieno[2,3-c]-furan-6-one
(102) 2-(4-Fluorophenyl)-3-(4-(aminosulfonyl)phenyl)-4H-thieno[2,3-c]-furan-6-one
(103) 2-(3,4-Difluorophenyl)-3-(4-(aminosulfonyl)phenyl)-4H-thieno[2,3-c]-furan-6-one
(104) 3-(4-(Methylsulfonyl)phenyl)-2-phenyl)-4,7-dihydrothieno[2,3-c]pyran-5-one
(105) 2-(4-(Methylsulfonyl)phenyl)-3-phenyl)-4H-thieno[2,3-c]furan-6-one
(106) 5-(4-(Methylsulfonyl)phenyl)-6-phenylimidazo[2,1-b]thiazole
(107) 2-Methyl-5-(4-(methylsulfonyl)phenyl)-6-phenylimidazo[2,1-b]thiazole
(108) 3-Methyl-5-(4-(methylsulfonyl)phenyl)-6-phenylimidazo[2,1-b]thiazole
(109) 2-Bromo-5-(4-(methylsulfonyl)phenyl)-6-phenylimidazo[2,1-b]thiazole
(110) 3-Trifluoromethyl-5-(4-(methylsulfonyl)phenyl)-6-phenylimidazo[2,1-b]thiazole
(111) 2,3-Dimethyl-5-(4-(methylsulfonyl)phenyl)-6-phenyl-imidazo[2,1-b]thiazole
(112) 5-(4-(Methylsulfonyl)phenyl)-6-(4-fluorophenyl)imidazo[2,1-b]thiazole
(113) 5-Phenyl)-6-(4-(methylsulfonyl)phenyl)-imidazo[2,1-b]thiazole
(114) 2-Chloro-5-(4-(methylsulfonyl)phenyl)-6-(4-chlorophenyl)imidazo[2,1-b]thiazole
(115) 2,2-Dichloro-5-(4-(methylsulfonyl)phenyl)-6-(4-chlorophenyl)imidazo[2,1-b]thiazole
(116) 5-(4-(Methylsulfonyl)phenyl)-6-phenylimidazo[2,1-b]-1,3,4-thiadiazole
(117) 5-Phenyl-6-(4-(methylsulfonyl)phenyl)imidazo[2,1-b]-1,3,4-thiadiazole
(118) 2-Methyl-5-(4-(methylsulfonyl)phenyl)-6-phenylimidazo[2,1-b]-1,3,4-thiadiazole
(119) 2-Methyl-5-phenyl-6-(4-(methylsulfonyl)phenyl)imidazo[2,1-b]-1,3,4-thiadiazole
(120) 5-(4-(Methylsulfonyl)phenyl)-6-(4-fluorophenyl)-imidazo[2,1-b]-1,3,4-thiadiazole
(121) 5-(4-(Methylsulfonyl)phenyl)-6-phenyl-1H-imidazo[2,1-b]-s-triazole
(122) 5-Phenyl-6-(4-(methylsulfonyl)phenyl)thiazolo[3,2-b]-1,3,4-triazole
(123) 2,3-Dihydro-5-(4-(methylsulfonyl)phenyl)6-phenylimidazo[2,1-b]thiazole
(124) 2-[(4-Methylthio)phenyl]-1-biphenyl
(125) 1-Cyclohexene-2-(4'-methylsulfonylphenyl)benzene
(126) 3-(4'-Methylsulfonylphenyl)-4-phenylphenol
(127) 1-[2-(4-Methylsulfonylphenyl)phenyl]piperidine
(128) 1-[2-(4'-Methylsulfonylphenyl)phenyl]pyrrole
(129) 1-Phenoxy-2-(4'-methylsulfonylphenyl)benzene
(130) 5-(4-fluorophenyl)-2-methoxy-4-[4-(methylsulfonyl)phenyl]-6-(trifluoromethyl)pyridine
(131) 2-Ethoxy-5-(4-fluorophenyl)-4-[4-(methylsulfonyl)phenyl]-6-(trifluoromethyl)pyridine
(132) 5-(4-Fluorophenyl)-4-[4-(methylsulfonyl)phenyl]-2-(2-propynyloxy)-6-(trifluoromethyl)pyridine
(133) 2-Bromo-5-(4-fluorophenyl)-4-[4-(methylsulfonyl)phenyl]-6-(trifluoromethyl)pyridine
(134) 3-[1-(p-Bromobenzyl)-5-methoxy-2-methylindol-3-yl]propanoic acid
(135) 3-[1-(p-Bromobenzyl)-5-methoxy-2-methylindol-3-yl]butanoic acid, sodium salt
(136) 2-Benzyl-3-[1-(p-bromobenzyl)-5-methoxy-2-methylindol-3-yl-propanoic acid
(137) 3-[1-(p-Bromobenzyl)-5-methoxy-2-methylindol-3-yl]-2,2-dimethylpropanoic acid
(138) 3-[1-(p-Bromobenzyl)-5-methoxy-2-methylindol-3-yl]-4,4,4-trifluorobutanoic acid, sodium salt
(139) trans-2-[1-(p-Bromobenzyl)-5-methoxy-2-methylindol-3-yl]-cyclopropanecarboxylic acid, sodium salt
(140) 3-[1-(p-Bromobenzyl)-5-methoxy-2-methylindol-3-yl]-hydroxy-2-methylpropanoic acid, sodium salt
(141) [1-(1-(p-Bromobenzyl)-5-methoxy-2-methylindol-3-yl]-cyclopropylacetic acid, sodium salt
(142) trans-(+)-2-[1-(p-Bromobenzyl)-5-methoxy-2-methylindol-3-yl]cyclopropanecarboxylic acid, sodium salt
(143) 3-[1-(p-Bromobenzyl)-5-methoxy-2-methylindol-3-yl]-2-methylpropanoic acid and sodium salt
(144) 3-[1-(p-Chlorobenzyl)-5-methoxy-2-methylindol-3-yl]-4,4,4-trifluorobutanoic acid and sodium salt
(145) syn-3-[1-(p-Bromobenzyl)-5-methoxy-2-methylindol-3-yl]-2-methylbutanoic acid
(146) anti-3-[1-(p-Bromobenzyl)-5-methoxy-2-methylindol-3-yl]-2-methylbutanoic acid and sodium salt
(147) 3-[5-(Bromo-1-(p-bromobenzyl)-2-methylindol-3-yl]butanoic acid and sodium salt
(148) (−)-3-[1-(p-Bromobenzyl)-5-methoxy-2-methylindol-3-yl]-butanoic acid and sodium salt
(149) (+)3-[1-(p-Bromobenzyl)-5-methoxy-2-methylindol-3-yl]-butanoic acid and sodium salt (150) trans-(−)-2-[1-(p-Bromobenzyl)-5-methoxy-2-methylindol-3-yl]cyclopropanecarboxylic acid and sodium salt
(151) 3-[1-(p-Bromobenzyl)-2,5-dimethylindol-3-yl]propanoic acid
(152) 3-[5-(Bromo-1-(p-bromobenzyl)-2-methylindol-3-yl]propanoic acid
(153) 3-[1-(p-Bromobenzyl)-5-chloro-2-methylindol-3-yl)propanoic acid
(154) 3-[1-(p-Chlorobenzyl)-5-methoxy-2-methylindol-3-yl)-2-methylpropanoic acid
(155) Methyl 3-[1-(p-bromobenzyl)-5-methoxy-2-methylindol-3-yl)propanoate
(156) 3-[1-(p-Bromobenzyl)-5-methoxy-2-methylindol-3-yl)-3-methylbutanoic acid
(157) 5-Methanesulfonamido-6-(2,4-difluorophenylthio)-1-indanone
(158) 5-Methanesulfonamido-6-(2,4-dichlorophenoxy)-1-indanone
(159) 2-(4-Chlorophenyl)-4-hydroxy-1-[4-(methylsulfonyl)phenyl]-4-(trifluoromethyl)-4,5-dihydro-1H-imidazole
(160) 2-(4-Chlorophenyl)-1-[4-(methylsulfonyl)phenyl]-4-(trifluoromethyl)-1H-imidazole
(161) 1-(4-Fluorophenyl)-4-hydroxy-2-[4-(methylsulfonyl)phenyl]-4-(trifluoromethyl)-4,5-dihydro-1H-imidazole
(162) 1-(4-Fluorophenyl)-2-[4-(methylsulfonyl)phenyl]-4-(trifluoromethyl)-1H-imidazole
(163) 2-(4-Chlorophenyl)-1-[4-methylsulfonyl)phenyl]-4-methyl-1H-imidazole
(164) 2-(4-Chlorophenyl)-1-[4-methylsulfonyl)phenyl]-4-phenyl-1H-imidazole
(165) 2-(4-Chlorophenyl)-4-(4-fluorophenyl)-1-[4-(methylsulfonyl)phenyl]-1H-imidazole
(166) 4-(4-Bromophenyl)-2-(4-chlorophenyl)-1-[4-(methylsulfonyl)phenyl]-1H-imidazole
(167) 2-(4-Chlorophenyl)-1-[4-(methylsulfonyl)phenyl]-4-(2-naphthyl)-1H-imidazole
(168) 2-(4-Chlorophenyl)-1-[4-(methylsulfonyl)phenyl]-4-[4-(trifluoromethoxy)phenyl]-1H-imidazole
(169) 2,4-Bis(4-chlorophenyl)-1-[4-(methylsulfonyl)phenyl]-1H-imidazole
(170) 2-(4-Chlorophenyl)-4-(3-chlorophenyl)-1-[4-(methylsulfonyl)phenyl]-1H-imidazole
(171) 2-(4-Chlorophenyl)-4-(4-methoxyphenyl)-1-[4-(methylsulfonyl)phenyl]-1H-imidazole
(172) 2-(4-Chlorophenyl)-4-(3-fluorophenyl)-1-[4-(methylsulfonyl)phenyl]-1H-imidazole
(173) 2-(4-Chlorophenyl)-4-[(4-chlorophenoxy)methyl]-1-[4-(methylsulfonyl)phenyl]-1H-imidazole
(174) 2-(3-Chloro-4-methylphenyl)-1-[4-(methylsulfonyl)phenyl]-4-(trifluoromethyl)-1H-imidazole
(175) 5-[1-[4-(Methylsulfonyl)phenyl)-4-(trifluoromethyl)-1H-imidazole-2-yl]-1,3-benzodioxole
(176) 2-(3-Fluoro-4-methoxyphenyl)-1-[4-(methylsulfonyl)-phenyl-4-(trifluoromethyl)-1H-imidazole
(177) 2-(4-Chlorophenyl)-4-[(phenylthio)methyl]-1-[4-(methylsulfonyl)phenyl]-1H-imidazole
(178) 2-(4-Chlorophenyl)-4-[(N-methyl-N-phenylamino)methyl]-1-[4-(methylsulfonyl)phenyl]-1H-imidazole
(179) 2-(4-Chlorophenyl)-4-[2-quinolyl)methoxymethyl]-1-[4-(methylsulfonyl)phenyl]-1H-imidazole
(180) 2-(4-Chlorophenyl)-4-methoxymethyl-1-[4-(methylsulfonyl)phenyl]-1H-imidazole
(181) 2-(4-Fluorophenyl)-1-[4-(methylsulfonyl)phenyl]-4-trifluoromethyl-1H-imidazole
(182) 1-[4-(Methylsulfonyl)phenyl]-2-phenyl-4-trifluoromethyl-1H-imidazole
(183) 2-(3-Chloro-4-methoxyphenyl)-1-[4-(methylsulfonyl)phenyl]-4-trifluoromethyl-1H-imidazole
(184) 2-(4-Methylphenyl)-1-[4-(methylsulfonyl)phenyl]-4-trifluoromethyl-1H-imidazole
(185) 1-[4-(Methylsulfonyl)phenyl]-2-(4-trifluoromethylphenyl)-4-trifluoromethyl-1H-imidazole
(186) 4-[2-(4-Chlorophenyl)-4-(trifluoromethyl)-1H-imidazol-1-yl]benzenesulfonamide
(187) 4-[2-(3-Chloro-4-methylphenyl)-4-(trifluoromethyl)-1H-imidazol-1-yl]benzenesulfonamide
(188) 3-[1-(4-Methylsulfonyl)phenyl]-4-trifluoromethyl-1H-imidazol-2-yl]pyridine
(189) 2-[1-(4-Methylsulfonyl)phenyl]-4-trifluoromethyl-1H-imidazol-2-yl]pyridine
(190) 4-[1-[4-(Methylsulfonyl)phenyl]-4-trifluoromethyl-1H-imidazol-2-yl]pyridine
(191) 2-Methyl-5-[1-[4-(methylsulfonyl)phenyl]-4-trifluoromethyl-1H-imidazol-2-yl]pyridine
(192) 2-Methyl-6-[1-[4-(methylsulfonyl)phenyl]-4-trifluoromethyl-1H-imidazol-2-yl]pyridine
(193) 5-Methyl-2-[1-[4-(methylsulfonyl)phenyl]-4-trifluoromethyl-1H-imidazol-2-yl]pyridine
(194) 4-Methyl-2-[1-[4-(methylsulfonyl)phenyl]-4-trifluoromethyl-1H-imidazol-2-yl]pyridine
(195) 2-Methoxy-5-[1-[4-(methylsulfonyl)phenyl]-4-trifluoromethyl-1H-imidazol-2-yl]pyridine
(196) 4-[2-(6-Methylpyridin-3-yl)-4-(trifluoromethyl)-1H-imidazol-1-yl]benzenesulfonamide
(197) 4-[2-(6-Methylpyridin-2-yl)-4-(trifluoromethyl)-1H-imidazol-1-yl]benzenesulfonamide
(198) 3-Methyl-5-[1-[4-(methylsulfonyl)phenyl]-4-(trifluoromethyl)-1H-imidazol-2-yl]pyridine
(199) 4-[2-(4-Methylpyridin-2-yl)-4-(trifluoromethyl)-1H-imidazol-1-yl]benzenesulfonamide
(200) 2-[1-[4-(Methylsulfonyl)phenyl]-4-(trifluoromethyl)1H-imidazol-2-yl]thiophene
(201) 3-[1-[4-(Methylsulfonyl)phenyl]-4-(trifluoromethyl)-1H-imidazol-2-yl]thiophene
(202) 4-[2-(5-Methylpyridin-3-yl)-4-(trifluoromethyl)-1H-imidazol-1-yl]benzenesulfonamide
(203) 2-Methyl-3-[1-[4-(methylsulfonyl)phenyl]-4-(trifluoromethyl)-1H-imidazol-2-yl]thiophene
(204) 4-[2-(2-Methylpyridin-3-yl)-4-(trifluoromethyl)-1H-imidazol-1-yl]benzenesulfonamide
(205) 4-[2-Pyridin-3-yl)-4-(trifluoromethyl)-1H-imidazol-1-yl]benzenesulfonamide The synthesis of compounds 1–39 is disclosed in Talley et al. U.S. Pat. No. 5,466,823. The synthesis of compounds 40 and 41 is disclosed in Black et al. U.S. Pat. No. 5,436,265. The synthesis of compounds 42–94 is disclosed in Ducharme et al. U.S. Pat. No. 5,474,995. The synthesis of compounds 95–105 is disclosed in Prasit et al. U.S. Pat. No. 5,521,213. The synthesis of compounds 106–123 is disclosed in Gauthier et al. U.S. Pat. No. 5,552,422. The synthesis of compounds 124–129 is disclosed in Batt U.S. Pat. No. 5,593,994. The synthesis of compounds 130–133 is disclosed in Lee U.S. Pat. No. 5,596,008. The synthesis of compounds 134–156 is disclosed in Lau et al. U.S. Pat. No. 5,604,253. The synthesis of compounds 157 and 158 is disclosed in Guay et al. U.S. Pat. No. 5,604,260. The synthesis of compounds 159–205 is disclosed in Khanna et al. U.S. Pat. No. 5,616,601.

Other selective inhibitors of cyclooxygenase-2 and their synthesis are taught in Examples 2–108, 110–129, 131–150, 152, 301–312, and 401–413 of Batt et al. U.S. Pat. No. 5,593,994, the disclosure of which is incorporated herein by reference. Still other selective inhibitors of cyclooxygenase-2 and their synthesis are taught in Examples 1–11, 13–16, and 18–25 of Guay et al. U.S. Pat. No. 5,604,260, the disclosure of which is incorporated herein by reference. Still other selective inhibitors of cyclooxygenase-2 and their synthesis are taught in Examples 1–13 including Examples 1a–1p and 4a-4h of Talley et al. U.S. Pat. No. 5,633,272, the disclosure of which is incorporated herein by reference. Still other selective inhibitors of cyclooxygenase-2 are taught in Examples 1–131 of Lau et al. U.S. Pat. No. 5,639,780, the disclosure of which is incorporated herein by reference. Still other selective inhibitors of cyclooxygenase-2 are taught in Examples 1–6 of Talley et al. U.S. Pat. No. 5,643,933, the disclosure of which is incorporated herein by reference. Still other selective inhibitors of cyclooxygenase-2 are taught in Examples 1–4 of Lau et al. U.S. Pat. No. 5,510,368, the disclosure of which is incorporated herein by reference.

Preferred inhibitors of cyclooxygenase-2 for use herein are 4-[5-(4-chlorophenyl)-3-(trifluoromethyl)-1H-pyrazol-1-yl]benzenesulfonamide which is compound (1) set forth above and 4-[5-(4-methylphenyl)-3-(trifluoromethyl)-1H-pyrazol-1-yl]benzenesulfonamide which is compound (4) set forth above; it is believed the latter compound is celicoxib (Trade name Celebrex®). Another preferred selective inhibitor of cyclooxygenase-2 is Vioxx® which is MK-0966; it is compound (63) set forth above.

Other preferred selective inhibitors of cyclooxygenase-2 are inhibitors of cyclooxygenase-2 which directly and selectively inhibit the enzyme cyclooxygenase-2 and also inhibit the synthesis of cyclooxygenase-2 protein and also have antioxidant properties. These selective inhibitors of cyclooxygenase-2 preferably contain phenyl group with two or more substituents selected from the group consisting of hydroxy and $C_{1-4}$-alkoxy (e.g., methoxy) on the phenyl. Such compounds are embraced by generic description in various patents but no species of selective cyclooxygenase-2 inhibitor containing phenyl group with two or more hydroxy or alkoxy substituents is disclosed in any of said patents. The patents referred to are: Talley et al. U.S. Pat. No. 5,643,933; Talley et al. U.S. Pat. No. 5,633,272; Khanna et al. U.S. Pat. No. 5,616,601; Lee U.S. Pat. No. 5,596,008; Batt et al. U.S. Pat. No. 5,593,994; and Adams et al. U.S. Pat. No. 5,593,992. Specific compounds for this kind of selective inhibitor of cyclooxygenase-2 include, for example, 4-[5-methyl-3-[[(2,3-hydroxy)phenoxy]methyl]-1H-pyrazol-1-yl]benzenesulfonamide and 4-methyl-5-(4-methylsulfonyl)phenyl-2-[(2,3-hydroxy)phenoxy]methyl]oxazole and the corresponding compounds where methoxy or ethoxy replaces hydroxy. 4-[5-Methyl-3-[[(2,3-hydroxy)phenoxy]methyl]-1H-pyrazol-1-yl]benzenesulfonamide has the structure

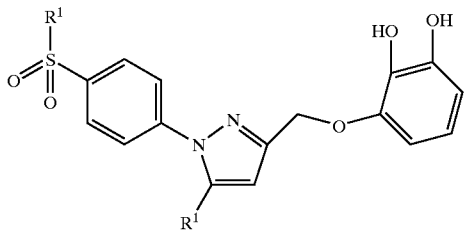

where $R^1$ is methyl and $R_2$ is $NH_2$. 4-(Methyl)-5-(4-methylsulfonyl)phenyl-2-[(2,3-hydroxyphenoxy)methyl]oxazole has the structure

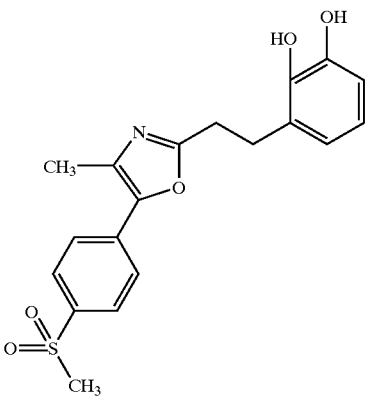

These compounds are embraced by broad disclosure in Talley et al. U.S. Pat. No. 5,643,933 but are not specifically disclosed therein. These compounds can be made analogously to Scheme XXII in U.S. Pat. No. 5,643,933 by reacting 2,3-dihydroxybenzyl bromide, where the hydroxy groups are protected by conventional techniques (for example, as described in E. Haslam, "Protection of Phenols and Catechols" pages 145–182, in Protective Groups in Organic Chemistry, McOmie, J. F. W., editor, Plenum Press, London (1973)), with alcohol corresponding to the product sought, in the presence of base, and deprotecting, and in the case of the methoxy or ethoxy compounds with alkoxy substituents in phenyl moiety, replacing the hydroxy substituents with alkoxy. Alternatively, these compounds can be made by reacting said alcohol with mesyl chloride to yield the unstable mesylate and then reacting with appropriate trihydroxyphenol. These compounds directly inhibit the cyclooxygenase-2 enzyme and also inhibit the synthesis of cyclooxygenase-2.

The dosage of selective inhibitor of cyclooxygenase-2 for the method of the broad embodiment herein is a cyclooxygenase-2 inhibiting amount which is a therapeutically effective amount, i.e., a cancer cell growth inhibiting amount. In general, the dosage ranges from 0.1 to 30 mg/kg. The dosages for any particular agent will vary within said range. For compound (4) referred to above, the dosage preferably ranges from 3 to 15 mg/kg, e.g., preferably is 12 mg/kg. For compound (63) referred to above, the dosage normally ranges from 12.5 to 50 mg daily. The route of administration is preferably systemic, e.g., oral or parenteral, e.g., intravenous.

We turn now to the embodiment directed at a method of treating breast cancer associated with overexpression of HER-2/neu in a patient affected with this condition comprising administering to said patient a therapeutically effective amount of a selective inhibitor of cyclooxygenase-2.

Primary treatment in the case of those determined to have breast cancer is mastectomy or breast conserving surgery (lumpectomy, tylectomy, wide excision, partial mastectomy, or quadrantectomy) plus radiation therapy.

Adjuvant systemic therapy is begun soon after primary therapy to delay recurrence and/or to prolong survival.

Breast cancer may metastasize to almost any organ in the body. Those most commonly involved include the lung, liver, bone, lymph nodes, and skin. Breast cancer also may metastasize to the central nervous system.

As indicated above, the invention herein is applicable to adjuvant therapy for HER-2/neu positive breast cancer and to treating HER-2/neu breast cancer that has metastasized.

The presence of HER-2/neu positive breast cancer is diagnosed by assays for HER-2/neu overexpression, e.g., as described above, carried out on breast cancer tissue.

The selective inhibitors of cyclooxygenase-2 for use in treating HER-2/neu positive breast cancer are those useful for treating cancers associated with the overexpression of HER-2/neu as described above and the dosages and routes of administration for these for treating HER-2/neu positive breast cancer are those described above in connection with treating cancers associated with the overexpression of HER-2/neu, and for adjuvant therapy for breast cancer, a therapeutically effective amount is a breast cancer cell growth inhibiting amount, and for treating breast cancer that has metastasized, a therapeutically effective amount is a metastatic cell growth inhibiting amount. For adjuvant therapy, administration is continued for two to five years. In the case of metastasized breast cancer, treatment is preferably continued until no further response is seen.

As indicated above, the inhibitors of cyclooxygenase-2 may be used as the sole treatment agent in treating HER-2/neu positive breast cancer. However, the inhibitors of cyclooxygenase-2 are preferably utilized in a combination regimen, for example, with HERCEPTIN®. When HERCEPTIN® is used as part of the therapy, a loading dose of 4 mg/kg IV is given followed by a weekly maintenance dose of 2 mg/kg IV. The inhibitors of cyclooxygenase-2 are also preferably used in combination regimen with standard therapy. One kind of standard adjuvant therapy is adjuvant chemotherapy, e.g., using a combination regimen of cyclophosphamide, methotrexate and 5-fluorouracil, e.g., for four to 24 months. Another kind of adjuvant systemic therapy is adjuvant tamoxifen therapy given for two to five years. Adjuvant chemotherapy is given routinely to all pre-menopausal, node-positive patients. Adjuvant tamoxifen therapy is given routinely to post-menopausal women who are node positive and have estrogen-receptor positive tumors. Standard therapies for patients with metastatic disease include endocrine therapy or chemotherapy or in some cases radiation therapy to palliate symptoms. Chemotherapies used for treating metastatic disease include paclitaxel (Taxol®) or a combination regimen of cyclophosphamide (Cytoxan®) and doxorubicin (Adriamycin®). Treatments herein for metastatic HER-2/neu positive breast cancer include a therapeutically effective amount of a selective inhibitor of cyclooxygenase-2 used in a combination regimen with HERCEPTIN® plus a conventional dosage of paclitaxel or used in a combination therapy with HERCEPTIN® plus a conventional dosage of cyclophosphamide and doxorubicin.

As indicated above, this application claims the benefit of U.S. Provisional Application No. 60/117,466. The entire disclosure of U.S. Provisional Application No. 60/117,466 is incorporated herein by reference.

The invention herein is illustrated by the following examples which are supported by the following background examples.

BACKGROUND EXAMPLE 1

Showing that HER-2/neu Oncogene Induces Cyclooxygenase-2 in Human Mammary Epithelial Cells The cells used were 184B5 and 184B5/HER cell lines. They were obtained from a collaborator. The 184B5 cell line is an immortalized but nontumorogenic human breast epithelial cell line that was established from a reduction mammoplasty and is described in Stampfer, M. R., et al., Proc. Natl. Acad. Sci. USA 82, 2394–2398 (1985). The 184B5/HER cell line was derived by stably transfecting 184B5 cells with a mutationally activated human HER-2/neu oncogene; these cells form rapidly growing tumors when injected into athymic nude mice. The 184B5/HER cell line is described in Pierce, J. H., et al., Oncogene 6, 1189–1194(1991). Cells were maintained in MEM (from Life Technologies, Inc. of Grand Island, N.Y.)—KBM, i.e., kerotinocyte basal medium (from Clonetics Corp. of San Diego, Calif.), mixed in a ratio of 1:1. The basal medium contained 10 ng/ml epidermal growth factor (EGF), 0.5 $\mu$g/ml hydrocortisone, 10 $\mu$g/ml transferrin, 5 $\mu$g/ml gentamicin and 10 $\mu$g/ml insulin. Cells were grown to 60% confluence, trypsinized with 0.05% trypsin–2 mM ethylenediamninetetraacetic acid (EDTA), and plated for experimental use.

Both cell lines were tested for production of prostaglandin $E_2$ ($PGE_2$) as follows: $5\times10^4$ cells/well were plated in 6-well dishes and grown to 60% confluence in the MEM-KBM mixed medium described above. Then the medium was replaced with fresh medium containing 10 $\mu$M sodium arachidonate. After 30 minutes, the medium was collected for analysis of $PGE_2$. The level of $PGE_2$ released by the cells was measured by enzyme immunoassay. Rates of production of $PGE_2$ were normalized to protein concentration. The results showed about 25 pg $PGE_2$/$\mu$g protein for 184B5 cell line and about 800 pg $PGE_2$/$\mu$g protein for 184B5/HER cell line or more than a ten-fold increase in production of $PGE_2$ in HER-2/neu—mediated transformed cells.

Western blotting was carried out to determine whether the differences in $PGE_2$ production were related to differences in amounts of COX enzymes. Western blotting was carried out as follows: Cell lysates were prepared by treating cells with lysis buffer (150 mM NaCl, 100 mM Tris (pH 8.0), 1% Tween 20, 50 mM diethyldithiocarbamate, 1 mM EDTA, 1 mM phenylmethylsulfonyl fluoride, 10 $\mu$g/ml aprotinin, 10 $\mu$g/ml trypsin inhibitor and 10 $\mu$g/ml leupeptin). Lysates were sonicated for 20 s on ice and centrifuged at 10,000 xg for 10 min to sediment the particulate material. The protein concentration of the supernatant was measured as described in Lowry, O. H., et al., J. Biol. Chem. 193, 265–275 (1951). SDS/PAGE was performed under reducing conditions on 10% polyacrylamide gels as described by Laemmli U. K, Nature 227, 680–685 (1970). The resolved proteins were transferred onto nitrocellulose sheets as detailed by Towbin, H., et al., Proc. Natl. Acad. Sci. USA 76, 4350–4354 (1979). The nitrocellulose membrane was then incubated with a rabbit polyclonal anti-COX-2 antiserum or a polyclonal anti-COX-1 antiserum. Secondary antibody to IgG conjugated to horseradish peroxidase was used. The blots were probed with the ECL Western blot detection system from Amersham of Arlington Heights, Ill., according to the manufacturer's instructions. The levels of COX-2 protein were much higher in the tumorigenic 184B5/HER cell line than in the nontumorigenic 184B5 partner cell line. COX-1 was not detectable by immunoblotting in these cell lines. The results indicate the differences in $PGE_2$ production were related to differences in amounts of COX-2 protein.

To investigate the mechanism responsible for differences in amounts of COX-2 protein, steady state levels of COX-2 mRNA were determined by Northern blotting for both cell lines. Northern blotting was carried out as follows: Total cellular RNA was isolated from cell monolayers using an RNA isolation kit from QIAGEN Inc. 10 $\mu$g of total cellular RNA per lane were electrophoresed in a formaldehyde-containing 1.2% agarose gel and transferred to nylon-supported membranes. After baking, membranes were pre-hybridized overnight in a solution containing 50% formamide, 5×sodium chloride-sodium phosphate-EDTA buffer (SSPE), 5×Denhardt's solution, 0.1% SDS and 100 $\mu$g/ml single-stranded salmon sperm DNA and then hybridized for 12 h at 42° C. with radiolabeled cDNA probes for human COX-2 and 18S rRNA. COX-2 and 18S rRNA probes were labeled with [$^{32}$P]-CTP by random priming. After hybridization, membranes were washed twice for 20 min at room temperature in 2×SSPE-0. 1% SDS, twice for 20 min in the same solution at 55° C., and twice for 20 min in 0.1×SSPE-0.1% SDS at 55° C. Washed membranes were then subjected to autoradiography. Consistent with the higher levels of COX-2 protein being obtained with higher levels of COX-2 gene expression, higher levels of COX-2 mRNA were detected in the 184B5/HER cells than in the 184B5 cells.

Nuclear run-offs were then carried out to determine if the HER-2/neu transformed cells provided increased rates of COX-2 transcription; i.e., whether differences in levels of mRNA reflected different rates of transcription. The nuclear run-off assays were carried out as follows: $2.5\times10^5$ cells were plated in four T150 dishes for each condition. Cells were grown in growth medium until approximately 60% confluent. Nuclei were isolated and stored in liquid nitrogen. For the transcription assay, nuclei ($1.0\times10^7$) were thawed and incubated in reaction buffer (10 mM Tris (pH 8), 5 mM $MgCl_2$, and 0.3 M KCl) containing 100 µCi of uridine 5'[$\alpha^{32}$P]triphosphate and 1 mM unlabeled nucleotides. After 30 min, labeled nascent RNA transcripts were isolated. The human COX-2 and 18S rRNA cDNAs were immobilized onto nitrocellulose and prehybridized overnight in hybridization buffer. Hybridization was carried out at 42° C. for 24 h using equal cpm/ml of labeled nascent RNA transcripts for each treatment group. The membranes were washed twice with 2×SSC buffer for 1 h at 55° C. and then treated with 10 mg/ml RNase A in 2×SSC at 37° C. for 30 min, dried and autoradiographed. Higher rate of synthesis of nascent COX-2 mRNA was observed in the transformed 184B5/HER cell line than in the nontransformed 184B5 counterpart.

Transient transfections were carried out with a series of human COX-2 promoter deletion constructs to confirm the nuclear run-off results by showing that COX-2 promoter activity was higher in 184B5/HER cells compared with 184B5 cells. The 184B5 and 184B5/HER cells were transfected with 1.8 µg of a series of COX-2 promoter-luciferase (−1432/+59, −327/+59, −220/+59, −124/+59, −52/+59) and 0.2 µg pSVβgal. Reporter activities were measured in cellular extract 24 hours later. Transient transfection assays were carried out as follows: 184B5 and 184B5/HER cells were seeded at a density of $5\times10^4$ cells/well in 6-well dishes and grown to 50–60% confluence. For each well, 2 µg of plasmid DNA were introduced using 8 µg of LipofectAMINE (from Life Technologies, Grand Island, N.Y.) as per the manufacturer's instructions. After 7 h of incubation, the medium was replaced with basal medium. The activities of luciferase and β-galactosidase were measured in cellular extract as described in Mestre, J. R., et al., Cancer Res. 57, 1081–1085 (1997). Luciferase activity was obtained representing data that was normalized to β-galactosidase activity. Six wells were used for each of the conditions. When the −1432/+59 COX-2 promoter construct (described in Inoue, H., et al., J. Biol. Chem. 270, 24965–24971 (1995)) was utilized, COX-2 promoter activity was about five-fold higher in 184B5/HER cells compared with 184B5 cells. Higher promoter activities for 184B5/HER cells than for 184B5 cells were also noted for the COX-2 promoter deletion constructs −327/+59, −220/+59 and −124/+59 (also described in Inoue, H., et al., J. Biol. Chem 270, 24965–24971 (1995)) but not for the −52/+59 construct (also described in Inoue, et al.). A CRE (cyclic AMP response element) is present between nucleotides −59 and −53 suggesting that this element may be responsible for mediating the effects of HER-2/neu.

To test whether the CRE is responsible for mediating the effects of HER-2/neu, transient transfections were carried out utilizing COX-2 promoter constructs in which specific enhancer elements including the CRE were mutagenized. 184B5 and 184B5/HER cells were transfected as described with 1.8 µg of a series of COX-2 promoter-luciferase constructs (−327/+59; KBM, ILM; CRM; CRM, ELM) and 0.2 µg pSVβgal. KBM represents the −327/+59 COX-2 promoter construct in which the NFκB site was mutagenized; ILM represents the −327/+59 COX-2 promoter construct in which the NF-IL6 site was mutagenized; CRM refers to the −327/+59 COX-2 promoter construct in which the CRE was mutagenized; CRM, ELM represents the −327/+59 COX-2 promoter construct in which both the NF-IL6 and CRE elements were mutagenized. Reporter activities were measured in cellular extract 24 h later. Luciferase activity represents data that have been normalized to β-galactosidase activity. Six wells were used for each of the conditions. The results were as follows; The increased COX-2 promoter activity detected in 184B5/HER cells was abrogated by mutagenizing the CRE site. By contrast, mutagenizing the NFκB and NF-IL6 sites had no effect on COX-2 promoter function.

Overexpressing HER-2/neu has been shown to activate Ras signaling. It is reasonable, therefore, to expect that the inductive effects of HER-2/neu on COX-2 are mediated by the Ras pathway. To determine if this is the case, testing was carried out to determine whether dominant negatives for different components of the Ras pathway block HER-2/neu mediated induction. The 1845B5 cell line was transfected with 0.9 µg of a human COX-2 promoter construct (−327/+59) (Control) and 0.2 µg pSVβgal. In case A, cells were co-transfected with 0.4 µg of expression vectors for HER-2/neu, Ras and dominant negative Ras. In Case B, cells were co-transfected with 0.4 µg of expression vectors for HER-2/neu, ERK1 or dominant negative ERK1. In case C, cells were co-transfected with 0.4 µg of expression vectors for HER-2/neu, c-Jun or dominant negative c-Jun. The total amount of DNA in each reaction was kept constant at 2 µg by using corresponding empty expression vectors. Luciferase data represents data that have been normalized to β-galactosidase activity. The results indicate that HER-2/neu and Ras oncogenes up-regulated COX-2 promoter activity. Furthermore, HER-2/neu-mediated stimulation of COX-2 promoter activity was suppressed by dominant negative Ras. Similarly, HER-2/neu-mediated induction of COX-2 promoter activity was inhibited by dominant negatives for ERK1 and c-Jun. These results indicate that the Ras pathway mediates the induction of COX-2 in HER-2/neu transformed cells.

To further investigate the effects of HER-2/neu on Ras signaling, measurement was carried out on levels of MAP (mitogen-activated protein) kinase activity, c-Jun and phosphorylated c-Jun in 184B5/HER and 184B5 cells.

The activity of p44/42 MAP kinase was measured using a nonradioactive method where the assay was performed with a p44/42 MAP kinase activity kit obtained from New England Biolabs (of Beverly, Mass.) using the manufacturer's instructions. Level of MAP kinase activity was higher in 184B5/HER cells than in its nontransformed 184B5 partner cell line. Treatment with PD 98059 (2'-amino-3'-methoxyflavone), a specific inhibitor of MAP kinase, caused a decrease in amounts of COX-2 in 184B5/HER cells. Similarly, SB 202190(4-(4-fluorophenyl)-2-(4- hydroxyphenyl)-5-(4-pyridyl)-1H-imidazole), a selective inhibitor of p38 MAP kinase, down-regulated amounts of COX-2 in 184B5/HER cells.

Levels of c-Jun and phosphorylated c-Jun were measured as follows: In case A, total cellular RNA was isolated from 184B5 (lane 1) and 184B5/HER (lane 2) cells. 10 μg of RNA was added to each lane. The blot was hybridized with probes that recognized c-Jun mRNA and 18S rRNA. The level of c-Jun mRNA was found to be higher in 184B5/HER cells compared to the nontransformed 184B5 partner cell line. In cases B and C, cellular lysate protein was prepared from 184B5 (lane 1) and 184B5/HER cells (lane 2) and loaded (50 μg/lane) onto a 10% SDS-polyacrylamide get. Following electrophoresis and transfer to nitrocellulose, the immunoblots were probed with antibodies to c-Jun and phosphorylated c-Jun, respectively. Levels of c-Jun and phosphorylated c-Jun were found to be higher in 184B5/HER cells compared to the nontransformed 184B5 partner cell fine. The above results indicate that HER-2/neu activates Ras signaling, which activates c-Jun which in turn induces COX-2 gene expression via the CRE site in the COX-2 promoter.

BACKGROUND EXAMPLE 2

HER-2/neu positive and HER-2/neu negative (no overexpressing of HER-2/neu in breast cancer tissue) breast cancer tissue samples were obtained from Memorial Sloan Kettering Cancer Center.

Immunohistochemistry for HER-2/neu was performed on formalin-fixed paraffin-embedded tissue sections using avidin-biotin-peroxidase as described in Hsu, H. M., et al., J. Histochem. Cytochem. 29, 577–580 (1981), which is incorporated herein by reference, with counterstain using hematoxylin. Pretreatment consisted of microwave heating for 5 minutes in 0.01 M citrate buffer. Anti-HER-2/neu antibody was used at a dilution of 1:1000; normal rabbit serum was used as the primary antibody for negative control sections. Immunoreactivity was scored as positive if greater than 20% of the tumor cells were reactive and intensity of signal was subjectively scored as 0 to 3$^+$ by usual examination. Cases scored as 2 or 3$^+$ were considered HER-2/neu positive; cases scored as 0 were considered HER-2/neu negative.

Analysis of the tissue samples for COX-2 was carried out as follows:

Ten mg of frozen human breast cancer tissue was thawed. The tissue was sonicated in 1 ml lysis buffer (150 mM NaCl 100 mM Tris (pH 8.0), 1% Tween 20, 50 mM diethyldithiocarbamate, 1 mM EDTA, 1 mM phenylmethylsulfonyl fluoride, 10 μg/ml aprotinin, 10 μg/ml trypsin inhibitor and 10 μg/ml leupeptin) and then centrifuged at 10,000×g for 10 minutes at 4° C. After discarding the pellet, the supernatant was then preabsorbed with 20 microliters of normal goat IgG and 20 microliters of rabbit IgG at 4° C.; twenty microliters of Protein G PLUS-Agarose was then added. The mixture was then centrifuged at 3,000×g for 5 minutes at 4° C. The pellet was discarded. Twenty microliters of rabbit anti-human COX-2 antiserum (Oxford Biomedical Research, Oxford, Mich., PG27) was then added to the supernatant; the mixture was then incubated at 4° C. on rocker platform for 1 hour. Twenty microliters of Protein A-Agarose was then added and the mixture was incubated on rocker platform for 16 hours at 4° C.; the mixture was then centrifuged at 3,000×g for 5 minutes at 4° C. The supernatant was discarded. After washing the pellet four times with RIPA buffer (PBS, 1% NP40, 0.5% sodium deoxycholate, 0.1% sodium dodecyl sulfate, 10 mg/ml phenylmethylsulfonyl fluoride, 10 μg/ml aprotinin, 100 mM sodium orthovanadate), the pellet was resuspended.

SDS/PAGE was performed under reducing conditions on 10% polyacrylamide gels. The resolved proteins were transferred onto a nitrocellulose sheet. The nitrocellulose membrane was then incubated with goat anti-human COX-2 antiserum (Santa Cruz Biotechnology, Inc., Santa Cruz, Calif. SC-1745). Secondary antibody to IgG conjugated to horseradish peroxidase was then used. The blots were probed with the ECL Western blot detection system according to the manufacturer's instructions (NEN Life Science Products Inc., Boston, Mass.).

COX-2 was detected in 14 of 15 HER-2/neu positive breast cancer tissue samples. It was not detected in 1 of 15 HER-2/neu positive breast cancer tissue samples. COX-2 was only detected in 4 of 14 HER-2/neu negative breast cancer tissue samples (P=0.0005); the levels of COX-2 were much lower in the four samples of HER-2/neu negative breast cancer tissue where COX-2 was detected than in any of the samples of HER-2/neu positive breast cancer where COX-2 was detected.

COX-2 was detected in 1 of 1 lymph nodes containing a HER-2/neu positive breast cancer metastasis. COX-2 was not detected in 2 of 2 lymph nodes containing HER-2/neu negative breast cancer metastases.

EXAMPLE I

A patient with HER-2/neu positive breast cancer is treated with Celebrex® for adjuvant therapy at an oral dose of 400 mg twice a day for five years after a mastectomy. Recurrence of breast cancer does not occur. The same result is obtained when the Celebrex® is replaced with an oral dose of 50 mg per day of Vioxx® for five years.

EXAMPLE II

A patient with HER-2/neu positive breast cancer is treated with Celebrex® or Vioxx® and HERCEPTIN® for adjuvant therapy. The patient received a loading dose of 250 mg intravenous HERCEPTIN®, then 10 weekly doses of 125 mg each IV. The patient also received an oral dose of 400 mg Celebrex® twice daily for one year or an oral dose of 50 mg Vioxx® daily for one year. Recurrence of breast cancer does not occur.

EXAMPLE III

Breast cancer is determined to have metastasized to lung and liver three years after a mastectomy is performed on a patient with HER-2/neu positive breast cancer. The patient is treated with oral doses of Celebrex® of 400 mg twice a day or of Vioxx® of 50 mg per day. A reduced tumor burden is noted.

After three months, the Celebrex® or Vioxx® was continued in combination regimen with Taxol® at a dose of 175 mg/m$^2$ administered intravenously every three weeks. A further reduced tumor burden is noted.

EXAMPLES IV

Breast cancer is determined to have metastasized to bone nine years after a mastectomy is performed on a patient with HER-2/neu positive breast cancer.

After failure of prior chemotherapy regimens, the patient is treated with Celebrex® at an oral dose of 400 mg twice a day or Vioxx® at an oral dose of 50 mg per day, and HERCEPTIN® at a loading dose of 250 mg IV followed by 10 weekly doses of 125 mg each TV. A reduced tumor burden is noted.

After 90 days, oral cyclophosphamide at a dose of 3 mg/kg/day and doxoribicin administered intravenously weekly at a dose of 20 mg/m², are added to the drug regimen. A still further reduced tumor burden is noted.

EXAMPLE V

A patient undergoes resection of colon cancer which proves to be HER-2/neu positive. The colon cancer is found to be localized to the bowel wall; there is no evidence of extracolonic cancer. The patient is treated with Celebrex® at oral dose of 400 mg twice a day for five years or an oral dose of Vioxx® at 50 mg per day for five years. Recurrence of colon cancer does not occur.

Many variations of the above will be obvious to those skilled in the art. Thus, the invention is defined by the claims.

What is claimed is:

1. A method for treating cancer associated with overexpression of HER-2/neu in a patient affected with this condition comprising administering to said patient a therapeutically effective amount of a selective inhibitor of cyclooxygenase-2 and a therapeutically effective amount of anti-HER-2/neu antibody.

2. A method for treating cancer associated with overexpression of HER-2/neu in a patient affected with this condition comprising administering to said patient a therapeutically effective amount of a selective inhibitor of cyclooxygenase-2 in combination regimen with another anti-HER-2/neu therapy.

3. The method of claim 1 where the cancer is HER-2/neu positive breast cancer.

4. The method of claim 1 where the cancer is HER-2/neu positive breast cancer and the inhibitor of cyclooxygenase-2 and the anti-HER-2/neu antibody are administered for or as part of adjuvant therapy.

5. The method of claim 4 where the inhibitor of cyclooxygenase-2 and the anti-HER-2/neu antibody are administered in combination regimen with other adjuvant therapy.

6. The method of claim 1 where the cancer is HER-2/neu positive breast cancer that has metastasized.

7. The method of claim 6 where the inhibitor of cyclooxygenase-2 and the anti-HER-2/neu antibody are administered in combination regimen with other therapy for the metastasized cancer.

8. The method of claim 2 where the cancer in HER-2/neu positive breast cancer.

9. The method of claim 8 where the inhibitor of cyclooxygenase-2 and the other anti-HER-2/neu therapy are administered for or as part of adjuvant therapy.

10. The method of claim 8 where the cancer is HER-2/neu positive breast cancer that has metastasized.

* * * * *